United States Patent
Nesper et al.

(10) Patent No.: US 8,696,676 B2
(45) Date of Patent: Apr. 15, 2014

(54) SURGICAL INSTRUMENT

(75) Inventors: Markus Nesper, Tuttlingen (DE);
Thomas Pleil, Bad Dürrheim (DE);
Klaus-Dieter Steinhilper, Tuttlingen
(DE); Dieter Weisshaupt, Immendingen
(DE)

(73) Assignee: Aesculap AG & Co. KG, Tuttlingen (DE)

( * ) Notice: Subject to any disclaimer, the term of this patent is extended or adjusted under 35 U.S.C. 154(b) by 134 days.

(21) Appl. No.: 13/314,968

(22) Filed: Dec. 8, 2011

(65) Prior Publication Data

US 2012/0101536 A1    Apr. 26, 2012

Related U.S. Application Data

(63) Continuation of application No. 11/205,132, filed on Aug. 17, 2005, now Pat. No. 8,096,999, which is a continuation of application No. PCT/EP2004/001346, filed on Feb. 13, 2004.

(30) Foreign Application Priority Data

Feb. 27, 2003 (DE) .................................. 103 10 004

(51) Int. Cl.
*A61B 17/56* (2006.01)
(52) U.S. Cl.
USPC ...................................................... 606/86 R
(58) Field of Classification Search
USPC ........................... 606/86 R, 99–105, 280–299
See application file for complete search history.

(56) References Cited

U.S. PATENT DOCUMENTS

| | | | |
|---|---|---|---|
| 4,617,846 A | 10/1986 | Horsch | |
| 5,397,361 A | 3/1995 | Clark | |
| 5,545,164 A | 8/1996 | Howland | |
| 5,669,912 A | 9/1997 | Spetzler | |
| 5,707,373 A | 1/1998 | Sevrain et al. | |
| 5,716,356 A | 2/1998 | Biedermann et al. | |
| 5,961,517 A | 10/1999 | Biedermann et al. | |
| 6,022,351 A | 2/2000 | Bremer et al. | |
| 6,059,678 A | 5/2000 | Suzuki | |

(Continued)

FOREIGN PATENT DOCUMENTS

| | | |
|---|---|---|
| DE | 197 00 404 | 7/1998 |
| DE | 298 12 988 | 11/1998 |

(Continued)

OTHER PUBLICATIONS

European Search Report, dated May 26, 2010, from related European Patent Application No. 10 148 084.3-2310.
International Preliminary Report on Patentability, dated Sep. 15, 2005, from related International Patent Application No. PCT/EP2004/001346.

*Primary Examiner* — Christopher Beccia
(74) *Attorney, Agent, or Firm* — Kenyon & Kenyon LLP

(57) ABSTRACT

A bone plate fixing device comprises a first bone contacting element with a rod-shaped connecting member and a second bone contacting element displaceable on the connecting member. The connecting member has a first portion with a first diameter and a second portion comprising a protruding projection, the protruding projection being located towards a proximal end of the connecting member and having a second diameter that is greater than the first diameter. The protruding projection may comprise at least two teeth. The depth of the at least two teeth may be less than half the difference between the first diameter and the second diameter.

20 Claims, 5 Drawing Sheets

(56) References Cited

U.S. PATENT DOCUMENTS

| | | |
|---|---|---|
| 6,258,091 B1 | 7/2001 | Sevrain et al. |
| 6,270,500 B1 | 8/2001 | Lerch |
| 6,379,363 B1 * | 4/2002 | Herrington et al. ............ 606/79 |
| 6,962,591 B2 | 11/2005 | Lerch |
| 7,255,700 B2 | 8/2007 | Kaiser et al. |
| 2002/0010475 A1 | 1/2002 | Lui |
| 2002/0052607 A1 | 5/2002 | Kennefick et al. |
| 2002/0156475 A1 * | 10/2002 | Lerch et al. .................... 606/70 |

FOREIGN PATENT DOCUMENTS

| | | |
|---|---|---|
| DE | 198 32 798 | 11/1999 |
| DE | 299 19 090 U1 | 1/2000 |
| DE | 198 32 797 | 2/2000 |
| EP | 0 857 466 A1 | 8/1998 |
| WO | 2004/028384 A1 | 4/2004 |
| WO | 2004/075765 A1 | 9/2004 |

* cited by examiner

SURGICAL INSTRUMENT

This application is a continuation of U.S. application Ser. No. 11/205,132 filed on Aug. 17, 2005, which is a continuation of International Application No. PCT/EP2004/001346 filed on Feb. 13, 2004, which claims priority of German Application No. 103 10 004.0 filed on Feb. 27, 2003. The entire disclosures of these prior applications are considered as being part of the disclosure of this application and are hereby incorporated in their entirety herein.

BACKGROUND OF THE INVENTION

The invention relates to a surgical instrument for applying a bone plate fixing device comprising a first bone contacting element with a rod-shaped connecting member projecting therefrom and defining a longitudinal direction, and a second bone contacting element displaceable on the connecting member in a direction towards the first bone contacting element, with a first tool element positionable in a contacting position on the second bone contacting element, and a second tool element removable from the first tool element, with a transportation device for stepwise transportation of the connecting member with the second tool element in several transportation steps in a proximal direction away from the first tool element resting in the contacting position on the second bone contacting element.

An instrument of the kind described at the outset is known, for example, from DE 197 00 474 C2. With a second tool element formed by two clamping jaws the rod-shaped connecting member can be clamped in a clamp position and moved in the clamp position relative to the second bone contacting element.

A subsequent grasping of the connecting member with the clamping jaws is possible in the above-described manner.

With the known instrument, however, a defined transportation of the connecting member relative to the second bone contacting element is not clearly ensured. Moreover, it is difficult to securely grasp a smooth connecting member. With structured connecting members there is the problem that a structure of the connecting member may dig into the clamping jaws and cause damage to these. In any case, when high pulling forces act on the second tool element there is the danger that the clamping jaws will slide off the connecting member. Furthermore, the instrument is difficult to clean when the clamping jaws have been damaged by sharp-edged structures of the connecting members.

The object underlying the present invention is therefore to so improve a surgical instrument of the kind described at the outset that the bone contacting elements of the fixing device can be displaced relative to each other in a simple way and the handling of the instrument is simplified.

SUMMARY OF THE INVENTION

This object is accomplished in accordance with the invention with a surgical instrument of the kind described at the outset in that the second tool element has several receptacles for a projection protruding from the connecting member, in that with each transportation step the projection is at least partially engageable with a receptacle in an engagement position and is held therein immovably in longitudinal direction on the second tool element, and in that from one transportation step to a following transportation step the projection is engageable with a receptacle arranged in a more proximal direction on the second tool element.

The instrument according to the invention makes it possible to pass the projection of the connecting member in a defined manner and with a pre-determined size of step through the instrument. The formation of receptacles for receiving the projection allows the receptacles to be made of an appropriately large size, so that the second tool element and thus the entire instrument can be cleaned well. In the engagement position, movement of the connecting member relative to the second tool element in longitudinal direction is not possible. As a result, the second tool element cannot slide off the connecting member which is held by means of the projection in a receptacle.

It is advantageous for the second tool element to be engageable in a distal position relative to the first tool element with the projection in the engagement position, for the second tool element to be movable in the engagement position in proximal direction from the distal position into a proximal position more removed from the first tool element, and for the second tool element to be transferable in the proximal position from the engagement position to a release position in which the second tool element and the projection are disengaged. An instrument constructed in this way allows the projection to be gripped with the second tool element and moved in proximal direction, so that the second bone contacting element resting against the first tool element is moved relative to the projection of the connecting member. To subsequently grasp the projection, i.e., grasp it again, with the second tool element, the engagement position can be released, i.e., the second tool element and the projection are displaceable again relative to each other in longitudinal direction. This is only possible in the release position.

It is advantageous for the second tool element to be movable in the release position from the proximal position to the distal position. The projection then maintains its position relative to the second bone contacting element, whereas the second tool element can be moved past the projection into the distal position. In this way, a stepwise transportation of the projection is realized with the instrument in proximal direction.

A particularly secure connection is obtained in the engagement position when the projection is insertable into the receptacles with a positive fit. When the projection corresponds in design to a receptacle, damage to the second tool element is excluded. Moreover, the second tool element can be cleaned in a simple way when the projection and the receptacle are designed so as to be sufficiently large in size.

In order to ensure that the projection is holdable on the second tool element immovably in longitudinal direction, it is advantageous for the second tool element to be movable transversely to the longitudinal direction relative to the projection. In this way, it allows, as it were, a locking of the projection on the second tool element.

The construction of the instrument is particularly simple when the second tool element comprises a first and a second clamping jaw and when at least one of the two clamping jaws carries the receptacles. In this way, the projection can be held between the two clamping jaws. It is, of course, also possible to provide both clamping jaws with receptacles, so that the projection can be held on both sides by receptacles of the clamping jaws.

In accordance with a preferred embodiment of the invention it can be provided that the second tool element comprises a toothing having a plurality of teeth, and that the toothing comprises the receptacles. This results in a particularly simple design of the second tool element.

It is conceivable to construct the projection in the form of a head. However, in order to improve a connection between the second tool element and the projection, the projection may comprise a projection toothing having at least two teeth. It is thus possible for a tooth of the toothing of the second tool element to selectively engage between the at least two teeth of the projection toothing. It is also conceivable for the projection as a whole, i.e., also its projection toothing having at least two teeth, to be insertable into a single receptacle of the toothing of the second tool element.

For transportation of the projection away from the second bone contacting element in a defined manner, it may be advantageous for the projection to be transportable over at least one transportation path in proximal direction from one transportation step to a following transportation step, and for the transportation path to correspond to the smaller of the tooth spacings of the toothing and the projection toothing. This makes it possible to predetermine a defined smallest transportation path by the shape of the toothing or the projection toothing. An actual transportation path or stroke may, of course, correspond to an integral multiple of the smallest transportation path.

To facilitate cleaning of the second tool element, it may be provided that the toothing of the second tool element has a pitch which corresponds to an integral multiple of a pitch of the toothing of the projection toothing. This results in particularly large spacings of the teeth of the toothing of the second tool element. In particular, a pitch ratio may be 2:1 or 3:1.

It is advantageous for the projection to have a holding receptacle for receiving at least one tooth of the toothing. This has the advantage that, on the one hand, the projection as a whole is insertable into a receptacle of the second tool element and, on the other hand, a tooth of the toothing is insertable into the holding receptacle. A double connection can thus be realized, for example, in the form of two positively engaging teeth and gaps between two teeth, respectively.

The construction of the device becomes particularly simple when the projection toothing comprises the holding receptacle.

To avoid a relative movement in longitudinal direction in the engagement position between the projection and the second tool element, it may be advantageous for the at least one tooth of the toothing to be introducible into the holding receptacle transversely to the longitudinal direction.

It is advantageous for the holding receptacle to comprise a ring groove. This can be produced in a particularly simple way on the projection or directly on the connecting member.

To avoid damage to the second tool element or to the connecting member, it is advantageous for the receptacles to be of edge-free design. The edge-free design has the further advantage that when entering a receptacle, the projection is guided by advantageous roundings of the receptacles into the receptacles.

In order for the projection not to cause any damage to the second tool element, it is advantageous for the projection to be of edge-free design. In this way, it can slide even better into a receptacle of the second tool element. In this respect rounded shapes of the projection are helpful.

For simple handling of the instrument it is advantageous for the instrument to comprise a main body and at least one actuating element movably mounted on the main body, and for a pulling force to be transmittable to the second tool element in longitudinal direction away from the first tool element by a movement of the actuating element relative to the main body. The tool element can thus be moved in a simple way in longitudinal direction.

In accordance with a preferred embodiment of the invention, it may be provided that a holding force is transmittable to the second tool element transversely to the longitudinal direction by a movement of the actuating element relative to the main body. This allows a holding force and a pulling force to be simultaneously exerted on the second tool element by the movement of the actuating element. Therefore an operator only has to move the actuating element and can thereby move the projection away from the first tool element.

It is advantageous for a force deflecting element to be provided for deflecting a pulling force acting in longitudinal direction into the holding force acting transversely to the longitudinal direction. By exerting a pulling force, not only the second tool element is moved in the direction of the pulling force, but simultaneously a holding force can be exerted on the connecting member, in particular on the projection, with the second tool element.

A particularly compact design is obtained for the instrument when the at least one clamping jaw rests against the force deflecting element and is guidable thereon during a movement of the force deflecting element in longitudinal direction. This may be realized by, for example, inclined slide surfaces on the force deflecting element. Furthermore, a force may be transmitted directly from the force deflecting element onto the at least one clamping jaw; further parts are not required therefor.

In order that pulling forces may be transmitted from the force deflecting element, it is advantageous ford pulling force to be transmittable to the force deflecting element from the at least one actuating element.

To avoid recoil or kickback of the second tool element on the instrument, it may be provided that the at least one clamping jaw is resiliently supported on the force deflecting element in longitudinal direction. As a result, it is always held under bias on the force deflecting element, whereby a particularly gentle application of the instrument is made possible.

In order to additionally absorb recoil forces, should the at least one actuating element be released abruptly, the force deflecting element may be resiliently supported on the main body.

Damage to the instrument may be effectively avoided when a pulling force limiter is provided for limiting the pulling force in longitudinal direction. Irrespective of how large a force is exerted on the actuating element by an operator, a maximum pulling force is limited by the pulling force limiter.

For limited transmission of forces from the actuating element onto the force deflecting element, it is advantageous for a force initiated by the at least one actuating element to be transmittable to a limited extent onto the force deflecting element by the pulling force limiter.

Particularly good damping properties are obtainable for the instrument when the force deflecting element is resiliently supported on the pulling force limiter.

In order to further improve the damping properties of the instrument, the pulling force limiter may be resiliently supported on the main body. Recoil forces which may occur when the at least one actuating element is abruptly released are attenuated by the resilient support.

In order to achieve a separation of a lifting movement and a pulling movement of the second tool element, it is advantageous for the at least one clamping jaw to be mounted on a push-and-pull element which is mounted on the main body for displacement in longitudinal direction, and for a pulling force to be transmittable onto the push-and-pull element from the at least one actuating element.

The following description of a preferred embodiment of the invention serves in conjunction with the drawings for a further explanation.

DETAILED DESCRIPTION OF THE INVENTION

Figure 1:
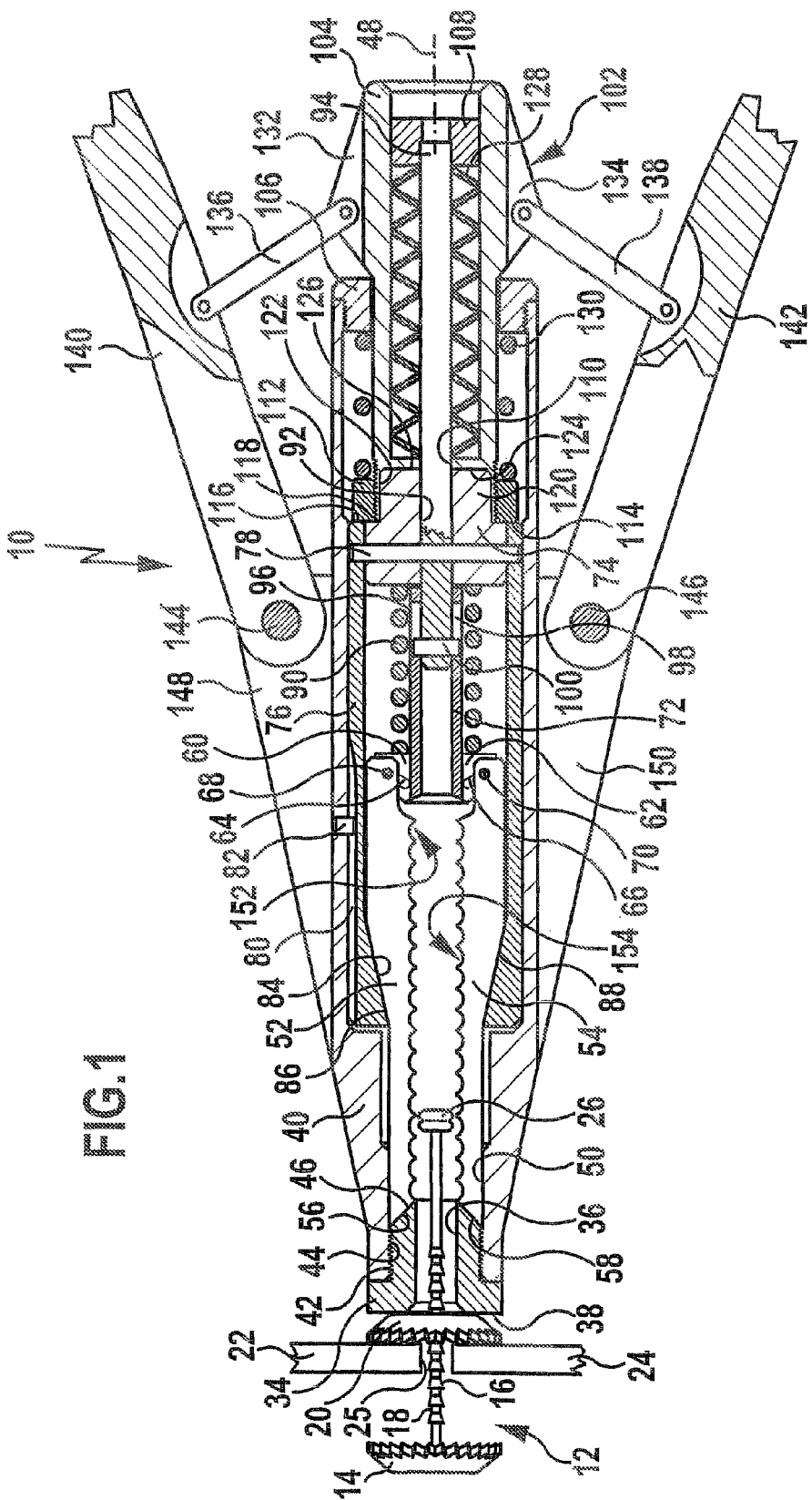
FIG. 1 shows tensioning pliers according to the invention with clamping jaws in a distal release position.

FIGS. 1 to 4 show an instrument according to the invention in the form of surgical tensioning pliers. The tensioning pliers 10 serve to apply a rivet-like fixing element 12 comprising a first contacting element 14 with an elongated shaft 18 having retaining projections 16 and protruding from the first contacting element 14, and a second contacting element 20 which is displaceable relative to the first contacting element 14 on the shaft 18 in the direction towards the first contacting element 14. Displacement of the second contacting element 20 relative to the first contacting element 14 away from the first contacting element 14 is not possible owing to the retaining projections 16 acting in this direction. Between the contacting elements 14 and 20 two separate bone portions 22 and 24 forming, for example, parts of a human skull bone may be attached to each other by the two contacting elements 14 and 20 clamping the bone portions 22 and 24 on either side thereof between them.

Arranged at an end of the shaft 18 pointing away from the first contacting element 14 is a ring-shaped projection 26 with a ring-shaped constriction 28. In this way, the projection 26 is, so to speak, provided with a toothing comprising two teeth 30 and 32.

A relative movement between the two contacting elements 14 and 20 is realizable by means of the tensioning pliers 10. For this purpose the tensioning pliers 10 comprise a first tool element in the form of a screw-in sleeve 34 which is provided with a longitudinal bore 36 and has a ring-shaped contact surface 38 pointing in distal direction for placement on the second contacting element 20. The longitudinal bore 36 is of such dimensions that the shaft 18 can be passed with the projection 26 through the screw-in sleeve 34.

The screw-in sleeve 34 is provided with an outer threaded section 42 which corresponds with an inner threaded section 44 at a distal end of a main body 40 of the tensioning pliers 10. At its proximal end the screw-in sleeve 34 has a conical surface 46 pointing in proximal direction. A tip of a cone defined by the conical surface 46 would lie on a longitudinal axis 48 of the tensioning pliers 10, which simultaneously forms an axis of symmetry of the tensioning pliers 10 and the fixing element 12.

The main body 40 is in the form of an elongated sleeve and has a ring-shaped contact section 50 adjoining the conical surface 46 for two elongated clamping jaws 52 and 54 arranged symmetrically in relation to the longitudinal axis 48. At the distal end, the clamping jaws 52 and 54 are each provided with an inclined slide surface 56 and 58, respectively, corresponding with the conical surface 46. At the proximal end, free ends of the clamping jaws 52 and 54 are mounted both pivotably and displaceably on bearing lugs 60 and 62, namely by a pin 68 and 70, respectively, orientated in a rotationally fixed manner on the clamping jaws 52 and 54, respectively, transversely to the longitudinal axis 48, extending through a slot 64 and 66, respectively, pointing in proximal direction at an incline from the longitudinal axis 48 on the bearing lugs 60 and 62, respectively. At the distal end the bearing lugs 60 and 62 are arranged so as to protrude radially on a pulling sleeve 72, which at the proximal end is connected to a bearing journal 74 formed rotationally symmetrically in relation to the longitudinal axis 48. At the distal end, the bearing journal 74 is secured against rotation and axial displacement in a proximal end of a clamping sleeve 76 by means of a bolt 78 extending through both the bearing journal 74 and the clamping sleeve 76 transversely to the longitudinal axis 48.

The clamping sleeve 76 is axially displaceably mounted in the main body 40 and secured against rotation relative to the main body 40 by a longitudinal groove 80, which extends on the outside away from a proximal end of the clamping sleeve 76 and in which a securing pin 82 engages, which protrudes on the inside from the clamping sleeve 76 and points in the direction towards the longitudinal axis 48. At the distal end, the clamping sleeve 76 has a decreasing inner diameter, whereby a deflection surface 84 is formed, which points at an incline in proximal direction towards the longitudinal axis 48. The clamping jaws 52 and 54 have inclined slide surfaces 86 and 88, respectively, which correspond with the deflection surface 84 and, in an initial position shown in FIG. 1, rest essentially in their entirety on the deflection surface 84.

A spiral spring 90 surrounding the pulling sleeve 72 is supported, on the one hand, on the bearing lugs 60 and 62, and, on the other hand, on the bearing journal 74. The spiral spring 90 therefore presses the clamping jaws 52 and 54 in distal direction with their slide surfaces 86 and 88 against the deflection surface 84, and the slide surfaces 56 and 58 against the conical surface 46.

The bearing journal 74 has a central bore 92 in which a cylindrical elongated pulling bolt 94 is inserted and held rotationally fixedly and axially indisplaceably on the bearing journal 74 by means of the bolt 78. At the distal end, the pulling bolt 94 is displaceably mounted in the pulling sleeve 72, which has two guide slots 96 and 98, which extend parallel to the longitudinal axis 48 and in which a guide pin 100 extending through the pulling bolt 94 transversely to the longitudinal axis 48 engages and thereby holds the pulling sleeve 72 on the pulling bolt 94 so that it is axially displaceable and secured against rotation.

At the proximal end, the pulling bolt 94 is connected to a pulling force limiter generally designated by reference numeral 102. This comprises a bearing sleeve 104 which is axially displaceably guided for longitudinal displacement on a bearing ring 106 which is screwed into a proximal end of the main body 40. The bearing sleeve 104 guides in its interior a ring-shaped head 108 which is rotationally fixedly connected to a proximal end of the pulling bolt 94. At the distal end, the pulling bolt 94 is axially displaceably guided at a central axial sleeve bore 110.

Screwed onto a distal end of the bearing sleeve 104 on the outside is a stop ring 112, which forms a stop surface 114 pointing in distal direction. In the initial position shown in FIG. 1, a proximal end 116 of the clamping sleeve 76 and a ring projection 118 of the bearing journal 74 lie against the contact surface 114. A journal portion 120 which is of reduced diameter in relation to the ring projection 118 engages a corresponding cylindrical recess 122 of the bearing sleeve 104, which is open in distal direction. A proximal end 126 of the bearing journal 74 abuts on a bottom 124 of the recess 122, through which the sleeve bore 110 extends.

A plate spring block 128 surrounding the pulling bolt 94 is arranged in the bearing sleeve 104 and supported, on the one hand, on the bottom 124 and, on the other hand, on the head 108 and thereby holds the bearing journal 74 under bias in the recess 122. A further spiral spring 130 surrounding the bearing sleeve at its distal end is arranged inside the main body 40 and supported, on the one hand, on the stop ring 112 and, on the other hand, on the bearing ring 106. It therefore presses the bearing sleeve 104 in its entirety in distal direction.

At the proximal end, two bearing blocks 132 and 134 protruding radially are symmetrically arranged on the bearing sleeve 104, and a rod-shaped link 136 and 138, respectively, is pivotably mounted on each of these. The links 136 and 138 are also pivotably connected to a swivel grip 140 and 142, respectively. The swivel grips 140 and 142 are pivotably held on bearing lugs 148 and 150 protruding radially from the main body 40 by means of two hinge bolts 144 and 146, respectively, oriented transversely to the longitudinal axis 48.

Figure 5:
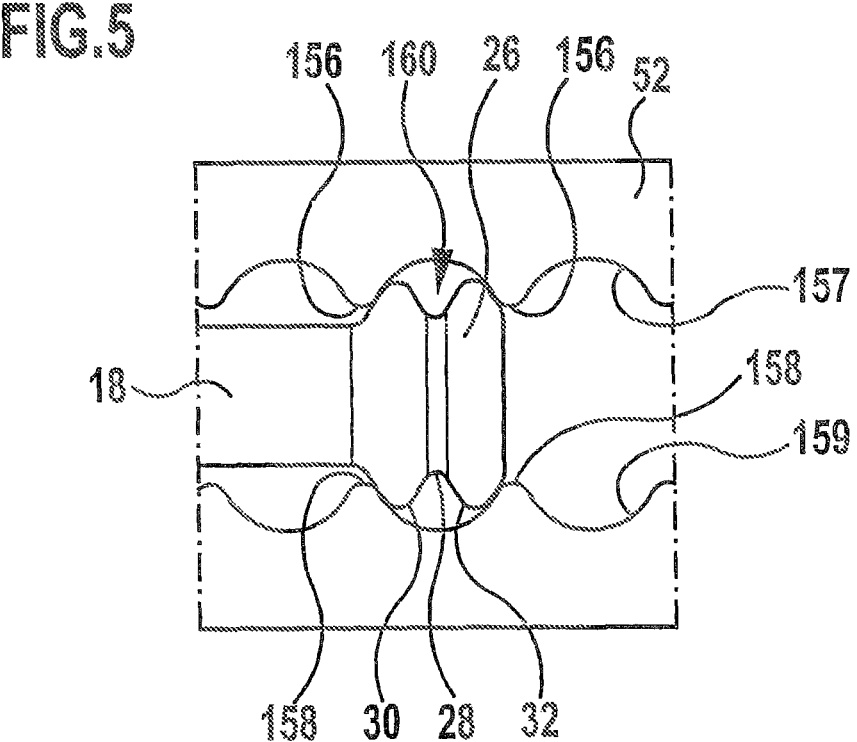
FIG. 5 shows a possible first engagement position of a projection of a connecting member on teeth of the clamping jaws.

The clamping jaws 52 and 54 are each provided with a toothing 152 and 154 respectively, which each have a plurality of teeth 156 and 158 pointing in the direction towards the longitudinal axis 48. Recesses constituting receptacles 157 and 159, respectively, are formed, in each case, between two teeth 156 and 158, respectively. The teeth 156 and 158 are all rounded. A spacing of the teeth 156 and 158 from each other is so selected that the projection 26 is introducible in its entirety between two teeth 156 and 158. Such an engagement position is shown in FIG. 5.

Figure 6:
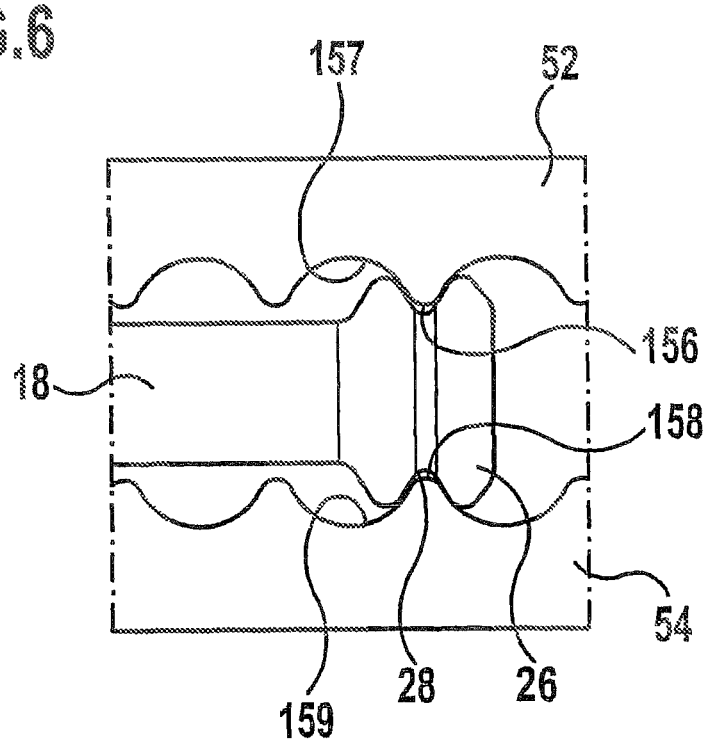
FIG. 6 shows a second possible engagement position of the projection on the teeth of the clamping jaws.

However, the shape of a tip of the teeth 156 and 158 also corresponds substantially to the shape of the constriction 28 of the projection 26 on the shaft 18, so that a tooth 156 and 158, respectively, of the clamping jaws 52 and 54 can respectively engage the constriction 28. Such an engagement position is shown in FIG. 6. The toothings 152 and 154 are so selected that the teeth 30 and 32 of the projection 26 are spaced half as far apart as two teeth 156 from each other and two teeth 158 from each other. Thus, a pitch of the toothings 152 and 154 corresponds to twice the pitch of the toothing 160 of the projection 26. Engagement positions, which correspond to half of the spacing of the pitch of the toothings 152 and 154 can therefore be defined. Two such engagement positions separated from each other at such a spacing are shown in FIGS. 5 and 6.

In conjunction with FIGS. 1 to 4 it will be explained in further detail hereinbelow how by means of the tensioning pliers 10 the second contacting element 20 may be displaced relative to the shaft 18 in the direction towards the first contacting element 14.

The two contacting elements 14 and 20 are first placed on either side of the two bone portions 22 and 24 to be joined together against these, and the shaft 18 is passed through a gap 25 in the bone. The shaft 18 with the projection 26 is introduced through the screw-in sleeve 34. The screw-in sleeve 34 is placed against the second contacting element 20. This initial position is shown in FIG. 1.

By swiveling the swivel grips 140 and 142 in the direction towards the longitudinal axis 48, the bearing sleeve 104 is pulled in proximal direction and presses the spiral spring 130 together. So long as the force exerted by the swivel grips 140 and 142 is smaller than the force exerted by the plate spring block 128, the bearing journal 74 is held in the recess 122 of the bearing sleeve 104. Together with the bearing journal 74 the clamping sleeve 76 is pulled in proximal direction, whereby the slide surfaces 86 and 88 of the clamping jaws 52 and 54 slide along the deflection surface 84 of the clamping sleeve 76. The deflection surface 84 therefore acts as a deflection element by means of which a pulling force acting in the direction of the longitudinal direction 48 is deflected into a pushing force in the direction towards the longitudinal axis 48. The clamping jaws 52 and 54 are moved with forced guidance in the direction towards the longitudinal axis 48, and guidance is effected, on the one hand, by the slide surfaces 56 and 58 lying against the conical surface 46, and, on the other hand, by the pins 68 and 70 guided in the slots 64 and 66

Figure 2:
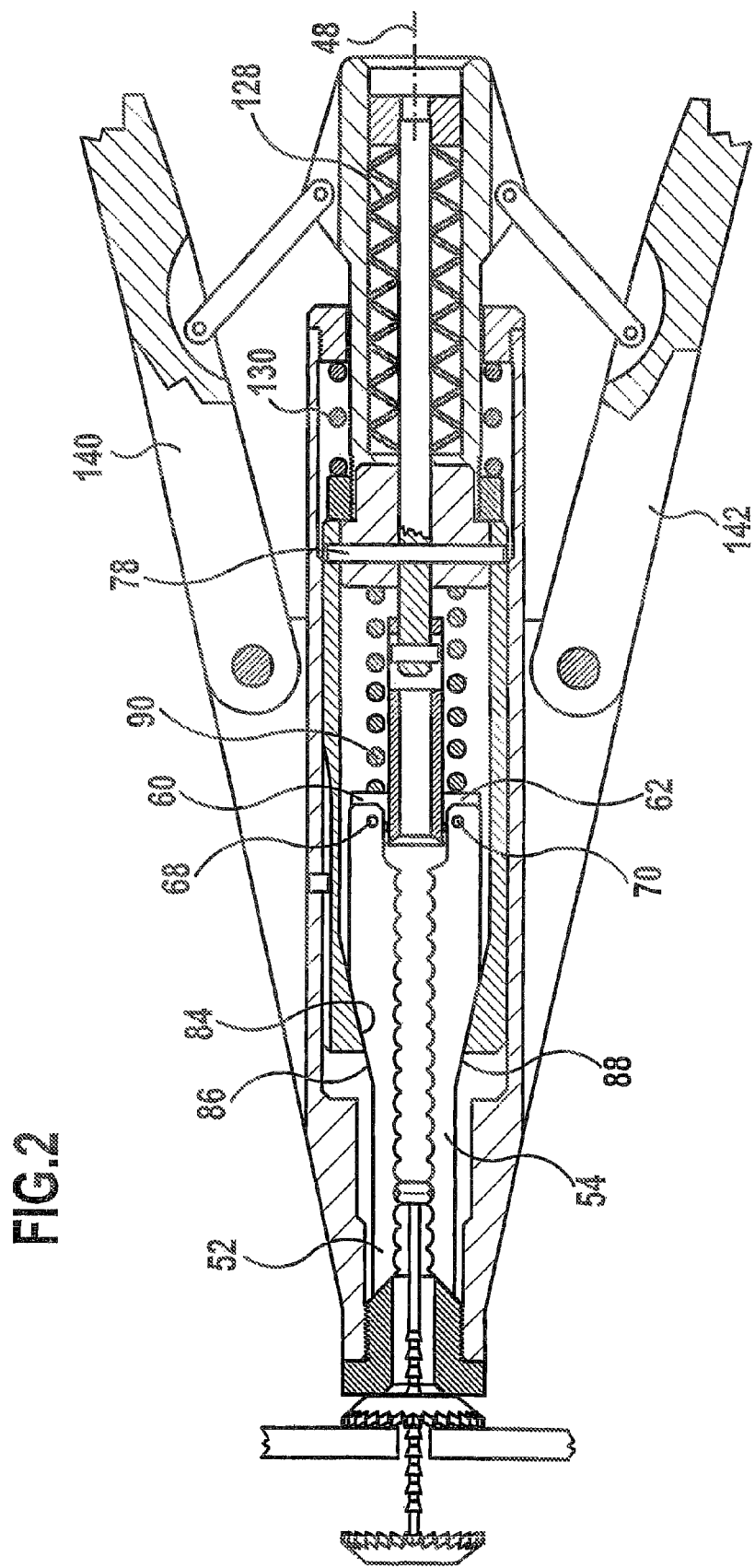
FIG. 2 shows the instrument of FIG. 1 with the clamping jaws in a distal engagement position.

The clamping jaws 52 and 54 can be moved in the direction towards the longitudinal axis 48 until the toothings 152 and 154 enter into engagement with the projection 26. For this purpose there are two engagement positions, which have already been explained in more detail in conjunction with FIGS. 5 and 6. FIG. 2 shows the engagement position of the clamping jaws 52 and 54 on the projection 26 in a distal position thereof. FIG. 5 corresponds to an enlarged detail from FIG. 2.

Figure 3:
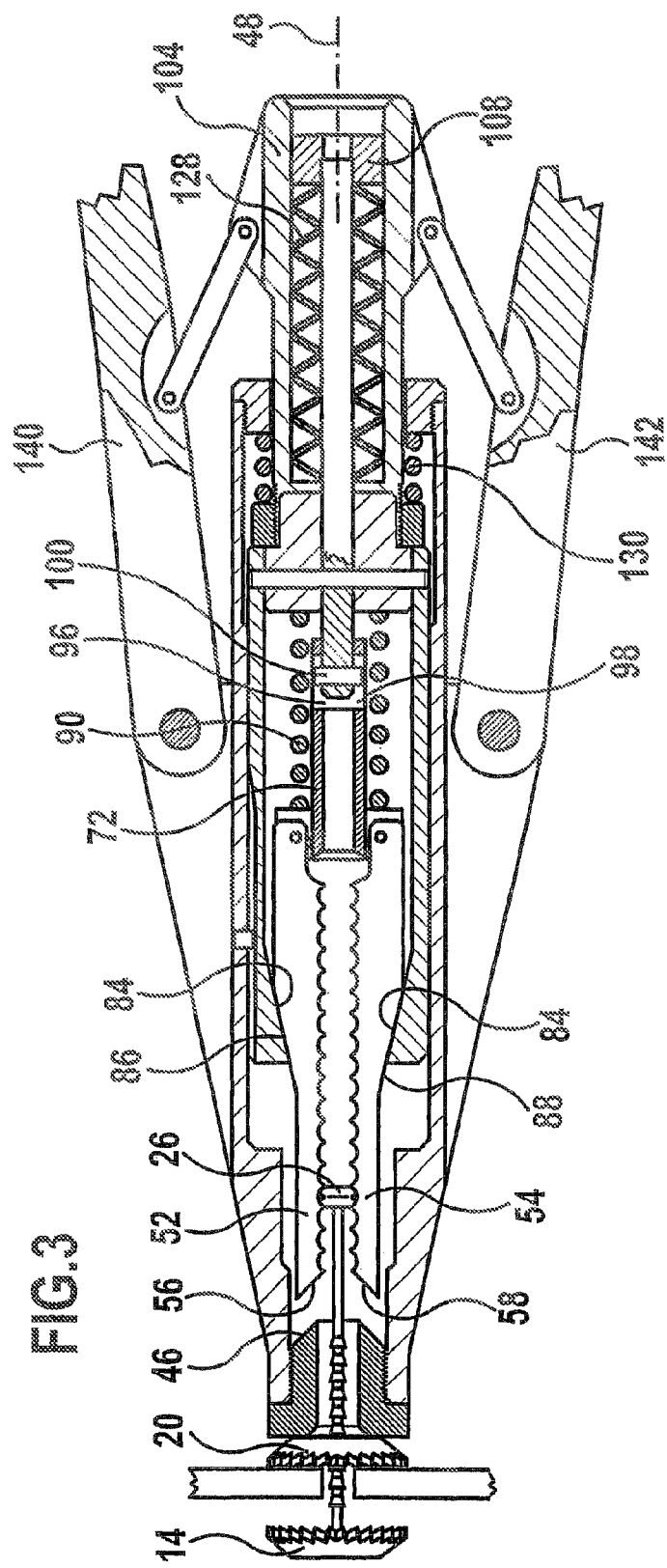
FIG. 3 shows the instrument of FIG. 1 with the clamping jaws in a proximal pull position.

When the swivel grips 140 and 142 are swiveled further in the direction towards the longitudinal axis 48, the clamping jaws 52 and 54 are taken along in proximal direction. The force of the spiral spring 90 is not sufficient to bias the clamping jaws 52 and 54 further in distal direction. FIG. 3 shows a position of the tensioning pliers 10 in which relative to the second contacting element 20 the projection 26 was moved away from the second contacting element 20, so that the second contacting element 20 already assumes a changed position in the direction towards the first contacting element 14.

Figure 4:
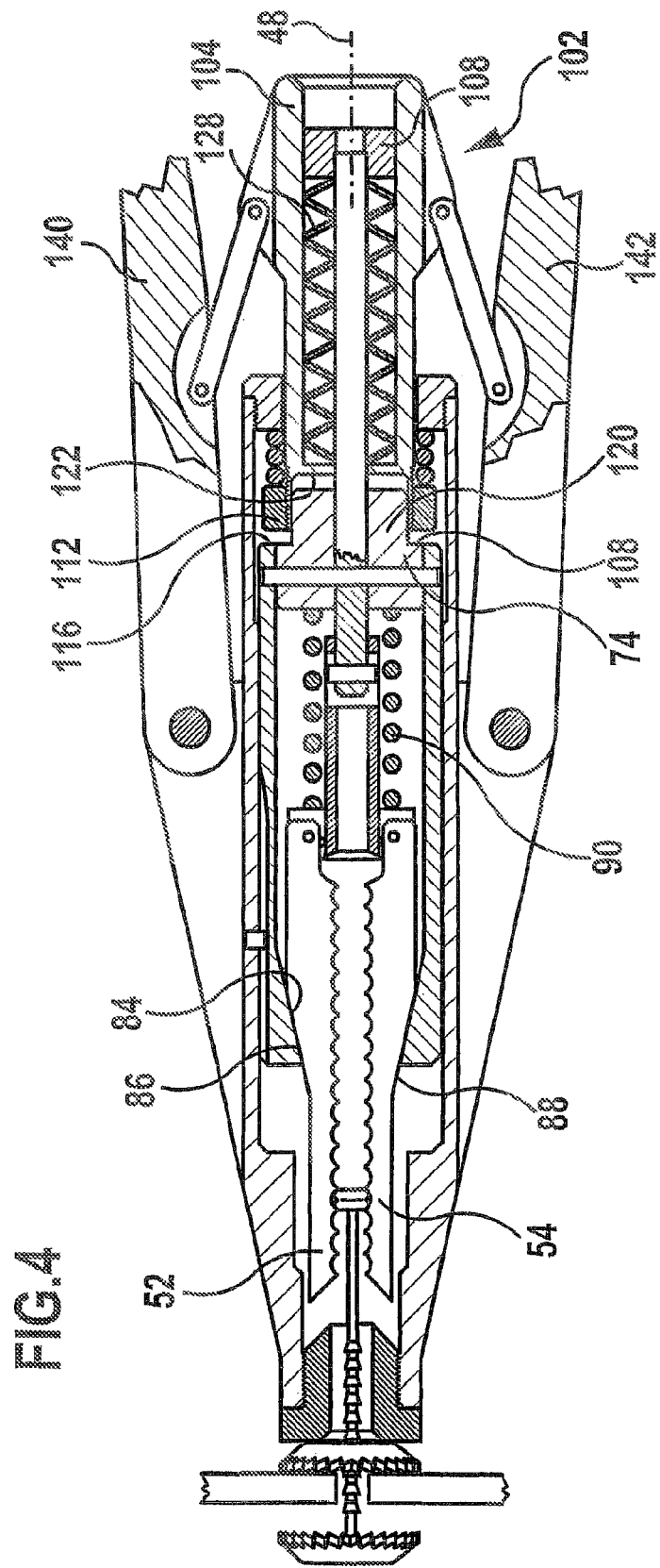
FIG. 4 shows the instrument of FIG. 3 with operative pulling force limiter.

When the swivel grips 140 and 142 are swiveled further in the direction towards the longitudinal axis 48, the pulling force limiter 102 begins to act. The pulling force exerted on the bearing sleeve 104 now exceeds the force exerted by the plate spring block 128, whereby the plate spring block 128 is compressed. An axial position of the clamping sleeve 76 relative to the main body 40 thereby remains practically constant. On the other hand, the spiral spring 130 as well as the plate spring block 128 are further compressed. This position is shown in FIG. 4.

To grasp the projection 26 with the clamping jaws 52 and 54 again, the swivel grips 140 and 142 are swiveled away from the longitudinal axis 48 again. This may occur automatically, for example, by means of a leaf spring, which is not shown. With appropriately chosen spiral springs 90 and 130, the arrangement of the tensioning pliers 10 makes it possible, in the pull position shown in FIG. 3, upon swiveling back the swivel grips 140 and 142 away from the longitudinal axis 48, for the clamping jaws 52 and 54 to first be moved radially away from the longitudinal axis 48 and from the projection 26 when the pull acting on the bearing sleeve 104 is reduced. As a result, the clamping jaws 52 and 54 release the projection 26 on the shaft 18. A further swiveling of the swivel grips 140 and 142 back into the initial position shown in FIG. 1 results in the clamping jaws 52 and 54 being moved in distal direction, but not being in engagement with the projection 26. Once the slide surfaces 56 and 58 come to rest against the conical surface 46 again, the projection 26 may be moved further in proximal direction in a further transportation step.

All in all, such a number of transportation steps are carried out in the above-described manner until the two bone portions 22 and 24 are held clamped between the two contacting elements 14 and 20.

We claim:

1. Bone plate fixing device comprising a first bone contacting element with a rod-shaped connecting member projecting from the first bone contacting element and defining a longitudinal direction, and a second bone contacting element displaceable on the connecting member in a direction towards the first bone contacting element, wherein the connecting member has a first portion over which the second bone contacting element is displaceable, the first portion having a first diameter, and a second portion comprising a protruding projection, the projection located towards a proximal end of the connecting member and having a second diameter that is greater than the first diameter;

wherein the protruding projection comprises at least two teeth; and wherein a depth of the at least two teeth is less than half the difference between the first diameter and the second diameter.

2. Bone plate fixing device in accordance with claim 1, wherein the projection is arranged at an end of the connecting member that points away from the first bone contacting element.

3. Bone plate fixing device in accordance with claim 1, wherein the projection is ring-shaped.

4. Bone plate fixing device in accordance with claim 1, wherein the projection has a ring-shaped constriction.

5. Bone plate fixing device in accordance with claim 1, wherein the projection has a holding receptacle for receiving at least one tooth of a toothing of an instrument.

6. Bone plate fixing device in accordance with claim 5, wherein the projection toothing comprises the holding receptacle.

7. Bone plate fixing device in accordance with claim 5, wherein the holding receptacle comprises a ring groove.

8. Bone plate fixing device in accordance with claim 1, wherein the projection is of edge-free design.

9. Bone plate fixing device in accordance with claim 1, wherein the projection is at least partly engageable with a receptacle of a surgical instrument for applying a bone plate fixing device in an engagement position and is held therein immovably in longitudinal direction.

10. Bone plate fixing device in accordance with claim 1, wherein the connecting member is in the form of an elongate shaft.

11. Bone plate fixing device in accordance with claim 1, wherein the connecting member has retaining projections, whereby a displacement of the second contacting element relative to the first contacting element away from the first contacting element is not possible owing to the retaining projections acting in this direction.

12. Bone plate fixing device in accordance with claim 1, wherein the bone plate fixing device is of rivet-like design.

13. Bone plate fixing device comprising a first bone contacting element with a rod-shaped connecting member projecting from the first bone contacting element and defining a longitudinal direction, and a second bone contacting element displaceable on the connecting member in a forward direction towards the first bone contacting element, wherein the connecting member has a first portion over which the second bone contacting element is displaceable, the first portion having a first diameter, and a second portion comprising a protruding projection, the projection located towards a proximal end of the connecting member and having a second diameter that is greater than the first diameter;

wherein the connecting member and the second contacting element are adapted to permit a displacement of the second contacting element on the connecting member in the forward direction towards the first bone contacting element by directly pushing the second contacting element in the forward direction while the second contacting element is on the connecting member.

14. Bone plate fixing device in accordance with claim 13, wherein the projection is arranged at an end of the connecting member that points away from the first bone contacting element.

15. Bone plate fixing device in accordance with claim 13, wherein the projection has a projection toothing comprising at least two teeth.

16. Bone plate fixing device in accordance with claim 13, wherein the projection is at least partly engageable with a receptacle of a surgical instrument for applying a bone plate fixing device in an engagement position and is held therein immovably in longitudinal direction.

17. Bone plate fixing device comprising a first bone contacting element with a rod-shaped connecting member projecting from the first bone contacting element and defining a longitudinal direction, and a second bone contacting element displaceable on the connecting member in a direction towards the first bone contacting element, wherein the connecting member has a first portion over which the second bone contacting element is displaceable, the first portion having a first maximum diameter, and a second portion comprising a protruding projection, the projection located towards a proximal end of the connecting member and having a second maximum diameter that is greater than the first maximum diameter, and wherein the protruding projection comprises at least two teeth.

18. Bone plate fixing device in accordance with claim 17, wherein the projection is arranged at an end of the connecting member that points away from the first bone contacting element.

19. Bone plate fixing device in accordance with claim 17, wherein the projection is at least partly engageable with a receptacle of a surgical instrument for applying a bone plate fixing device in an engagement position and is held therein immovably in longitudinal direction.

20. Bone plate fixing device in accordance with claim 17, wherein the connecting member has retaining projections, whereby a displacement of the second contacting element relative to the first contacting element away from the first contacting element is not possible owing to the retaining projections acting in this direction.

\* \* \* \* \*